US008480695B2

(12) United States Patent
Borghi et al.

(10) Patent No.: US 8,480,695 B2
(45) Date of Patent: Jul. 9, 2013

(54) DEVICE AND METHOD FOR ANASTOMOSIS

(75) Inventors: Enzo Borghi, Budrio (IT); Piergiorgio Tozzi, Lausanne (CH)

(73) Assignee: Newman Medical KFT, Budapest (HU)

( * ) Notice: Subject to any disclaimer, the term of this patent is extended or adjusted under 35 U.S.C. 154(b) by 193 days.

(21) Appl. No.: 12/941,301

(22) Filed: Nov. 8, 2010

(65) Prior Publication Data
US 2011/0066171 A1 Mar. 17, 2011

Related U.S. Application Data

(63) Continuation of application No. 11/018,777, filed on Dec. 21, 2004, now Pat. No. 7,837,697.

(30) Foreign Application Priority Data

Dec. 23, 2003 (IT) ............................... BO2003A0782

(51) Int. Cl.
*A61B 17/11* (2006.01)
(52) U.S. Cl.
USPC ......................................... 606/153; 285/340
(58) Field of Classification Search
USPC ........... 606/151–156; 285/65–79, 382–382.5, 285/417–419, 340
See application file for complete search history.

(56) References Cited

U.S. PATENT DOCUMENTS

| | | | |
|---|---|---|---|
| 2,635,901 A * | 4/1953 | Osborn | ........................... 285/33 |
| 3,254,650 A | 6/1966 | Collito | |
| 3,316,914 A | 5/1967 | Collito | |
| 3,357,432 A | 12/1967 | Sparks | |
| 3,679,241 A * | 7/1972 | Hoffmann | ...................... 285/340 |
| 4,214,586 A * | 7/1980 | Mericle | .......................... 606/154 |
| 4,366,819 A | 1/1983 | Kaster | |
| 4,368,736 A | 1/1983 | Kaster | |
| 4,500,117 A * | 2/1985 | Ayers et al. | ........................ 285/3 |
| 4,555,129 A | 11/1985 | Davlin | |
| 4,610,250 A | 9/1986 | Green | |
| 4,930,502 A | 6/1990 | Chen | |
| 4,931,057 A | 6/1990 | Cummings et al. | |

(Continued)

FOREIGN PATENT DOCUMENTS

DE 19725739 4/1999

OTHER PUBLICATIONS

Tozzi, P., et al., "Preliminary Clinical Experience With the Heartflo Anastomosis Device", Thorac. Cardiov. Surg., 2001, vol. 49, p. 279-282.

(Continued)

*Primary Examiner* — Kathleen Holwerda
(74) *Attorney, Agent, or Firm* — Pearne & Gordon LLP

(57) ABSTRACT

A device for forming an anastomosis of blood vessels or ducts includes a first inner cylindrical element for engaging a corresponding first blood vessel/prosthesis end portion and a first middle cylindrical element into which the first inner cylindrical element is inserted to bend the legs of the first inner cylindrical element inwards to a predetermined extent so that deformable legs thereof engage the vessel/prosthesis wall. The device includes a second inner cylindrical element for engaging a corresponding second blood vessel/prosthesis end portion and a second middle cylindrical element into which the second inner cylindrical element can be inserted to bend the legs of the second inner cylindrical element inwards to a predetermined extent so that deformable legs thereof engage the vessel/prosthesis wall. The device also includes an outer element for reciprocally connecting the first and second middle cylindrical elements.

11 Claims, 6 Drawing Sheets

U.S. PATENT DOCUMENTS

| | | |
|---|---|---|
| 5,089,008 A | 2/1992 | Chen |
| 5,123,908 A | 6/1992 | Chen |
| 5,217,474 A | 6/1993 | Zacca et al. |
| 5,250,058 A | 10/1993 | Miller et al. |
| 5,346,501 A | 9/1994 | Regula et al. |
| 5,366,462 A | 11/1994 | Kaster et al. |
| 5,697,943 A | 12/1997 | Sauer et al. |
| 5,916,226 A | 6/1999 | Tozzi |
| 5,951,576 A | 9/1999 | Wakabayashi |
| 6,030,392 A | 2/2000 | Dakov |
| 6,036,705 A | 3/2000 | Nash et al. |
| 6,086,608 A | 7/2000 | Ek et al. |
| 6,110,187 A | 8/2000 | Donlon |
| 6,443,501 B1 * | 9/2002 | Ketcham et al. ............ 285/319 |
| 6,451,034 B1 | 9/2002 | Gifford, III et al. |
| 6,551,334 B2 | 4/2003 | Blatter et al. |
| 6,652,540 B1 | 11/2003 | Cole et al. |
| 6,736,824 B2 | 5/2004 | Borghi |
| 6,893,452 B2 | 5/2005 | Jacobs |
| 7,267,680 B2 | 9/2007 | Wright |
| 2002/0173807 A1 | 11/2002 | Jacobs |
| 2005/0080437 A1 | 4/2005 | Wright |

OTHER PUBLICATIONS

Tozzi, P., et al., "Sutureless Coronary Anastomoses: Revival of Old Concepts", European Journal of Cardio-Thoracic Surgery, 2002, vol. 22, p. 565-570.

Tozzi, P., et al., "Is the Graftconnector a Valid Alternative to Running Suture in End-To-Side Coronary Arteries Anastomoses?", Ann. Thorac. Surg., 2001, vol. 72, p. S999-1003.

International Search Report mailed Aug. 1, 2005 for International application No. PCT/IB2004/004257.

International Preliminary Report on Patentability with Written Opinion issued Jun. 26, 2006 for International application No. PCT/IB2004/004257.

* cited by examiner

DEVICE AND METHOD FOR ANASTOMOSIS

CROSS-REFERENCE TO RELATED APPLICATION

This application is a continuation of U.S. application Ser. No. 11/018,777 filed Dec. 21, 2004 (Dec. 21, 2004), now U.S. Pat. No. 7,837,697, which claims priority from Italian application No. BO2003A000782 filed Dec. 23, 2003 (Dec. 23, 2003). The entire disclosure of U.S. application Ser. No. 11/018,777 filed Dec. 21, 2004 is hereby expressly incorporated by reference into the present specification.

BACKGROUND OF THE INVENTION

The present invention relates to a device and method for anastomosis.

In surgery, the term "anastomosis" is used to mean a connection made surgically between two hollow structures.

In particular, when the structures connected are the two ends of a blood vessel, a lymphatic vessel or other type of duct, the operation is called end-to-end anastomosis and its purpose is to restore flow to the vessel or duct.

The surgical connection between an end portion of a blood vessel to a side portion of a vessel wall, on the other hand, is termed "end-to-side anastomosis".

This specification expressly refers to vascular anastomosis applied to the human body, without thereby restricting the scope of the invention.

The earliest method of anastomosing two parts of a blood vessel or lymphatic vessel consists in suturing the free ends of the vessel with thread.

This method, commonly known as suture anastomosis, has several disadvantages, the main one being that the suture produces a scar which, however small, prevents original flow from being perfectly restored to the vessel.

In this connection, it should be stressed that blood vessels are made up of several layers. The first, innermost layer, called endothelium, is covered by a second, middle layer called tunica media. The tunica media is in turn covered by a third layer, known as tunica adventitia.

It is therefore relatively easy for suturing to cause misalignment of some kind between the layers of one end of the vessel and the corresponding layers of the end of the other vessel. This is also a drawback in the case of lymphatic vessels, which have a similar layered structure.

A second drawback is due to the fact that blood vessel suturing must be done by hand by a specialized surgeon because it is a complex operation that cannot be left to surgeons who are not highly skilled in this specific art.

Another known method of anastomosing two parts of a blood or lymphatic vessel is to use mechanical clamping devices designed to turn the ends to be connected inside out and to then join the inside walls of the vessel ends to each other.

This surgical technique (mechanical anastomosis by eversion), although simpler than suture anastomosis, is even less effective in restoring flow to the vessel.

For example, in the specific case of blood vessels, only the intimal layers are in contact with each other.

Besides this, mechanical anastomosis by eversion has other serious drawbacks which may be dangerous to the patients.

One drawback is due to the fact that everting the vessel ends may cause the ends to break, especially in the case of vessels larger than 3 mm in diameter whose walls are stiffened by arteriosclerosis.

Another complication, specific to blood vessels, is caused by the fact that the inside layers of the vessel ends, after being turned inside out and placed side by side, are no longer exposed to blood flow and therefore tend to atrophy, which in turn leads to narrowing of the blood vessel and reduction of the blood flow through it. The smaller the diameter of the vessel being operated on is, the more serious this problem is.

In other mechanical anastomosis methods (such as the one described in U.S. Pat. No. 6,652,540) the two ends of the vessels to be joined are not placed in contact and, instead, metallic components are left in contact with the blood flowing through the vessel. This produces an extremely dangerous condition which exposes the anastomosis to risk of immediate occlusion caused by the formation of a blood clot.

The prior patent application BO2000A000169, in the name of the same Applicant, describes an apparatus for end-to-end anastomosis in which the means for mutually connecting the vessel portions to be anastomosed enable the ends of the vessel to be held in place exactly so that the edges of the vessel match perfectly.

This solution solves many of the above mentioned problems thanks to its simple construction and to the fact that, once implanted, it enables the vessel to be reconstructed completely.

Although contamination of the blood due to contact with the connecting parts of the apparatus is less serious than in earlier solutions, the problem has not been totally solved, especially when the connecting parts are made of metal.

Indeed, it has been found that contact between metal and blood tends to cause stenosis, that is to say, abnormal narrowing of the blood vessel, which may lead to total occlusion of the vessel in a period of 6 months to 1 year.

Those in the art have proposed to overcome the problem by chemically coating the metals with anti-stenosis substances, that is to say, substances that inhibit occlusions.

This solution has, however, produced serious problems because in many cases, the chemically coated metal parts in contact with the blood favor the formation of thrombi and the onset of acute thromboses that come sharply to a crisis, exposing patients to the risk of heart failure and, in some cases, leading to death.

SUMMARY OF THE INVENTION

A first aim of the present invention is to provide a method and an apparatus for mechanical anastomosis that overcomes the problems caused by contact between the metal or artificial parts and the blood.

Another aim of the invention is to propose an anastomosis device that permits flow in the blood vessel to be re-established more effectively than prior art devices.

These aims are achieved by a device and method according to the main claims.

A first advantage of the invention is that contact between the connecting parts and the blood vessel is limited to the vessel wall, leaving the inside surface free, and there is therefore no contact with the blood inside the vessel.

Another advantage is that the layers making up the blood vessel are only partially broken which means that, after the operation, the vessel heals more quickly.

Yet another advantage is that the device supports the vessel wall radially from the outside at its front edge so that it maintains the required size and is prevented from contracting.

A yet further advantage is the absence of interference between the engagement means and the free front edge of the vessel, which, combined with the ability to keep the vessel at the required, measured size, permits an optimum connection between the different layers making up the anastomosed parts of the vessel.

A yet further aim of the invention is to propose a simplified anastomosis apparatus whose use can be learned in a very short time and which permits the formation of anastomoses of constant quality.

A still further aim of the invention is to propose an anastomosis apparatus that reduces the time required for the anastomosis operation.

BRIEF DESCRIPTION OF THE DRAWINGS

The invention will now be described with reference to the accompanying drawings which illustrate a preferred embodiment of it and in which:

FIGS. 4a and 4b are, respectively, a cross section similar to FIG. 2 but showing a different embodiment of the connecting means, and a detail view from above of an outer connecting cylinder of the apparatus of FIG. 4a;

DESCRIPTION OF THE PREFERRED EMBODIMENTS

Figure 1:
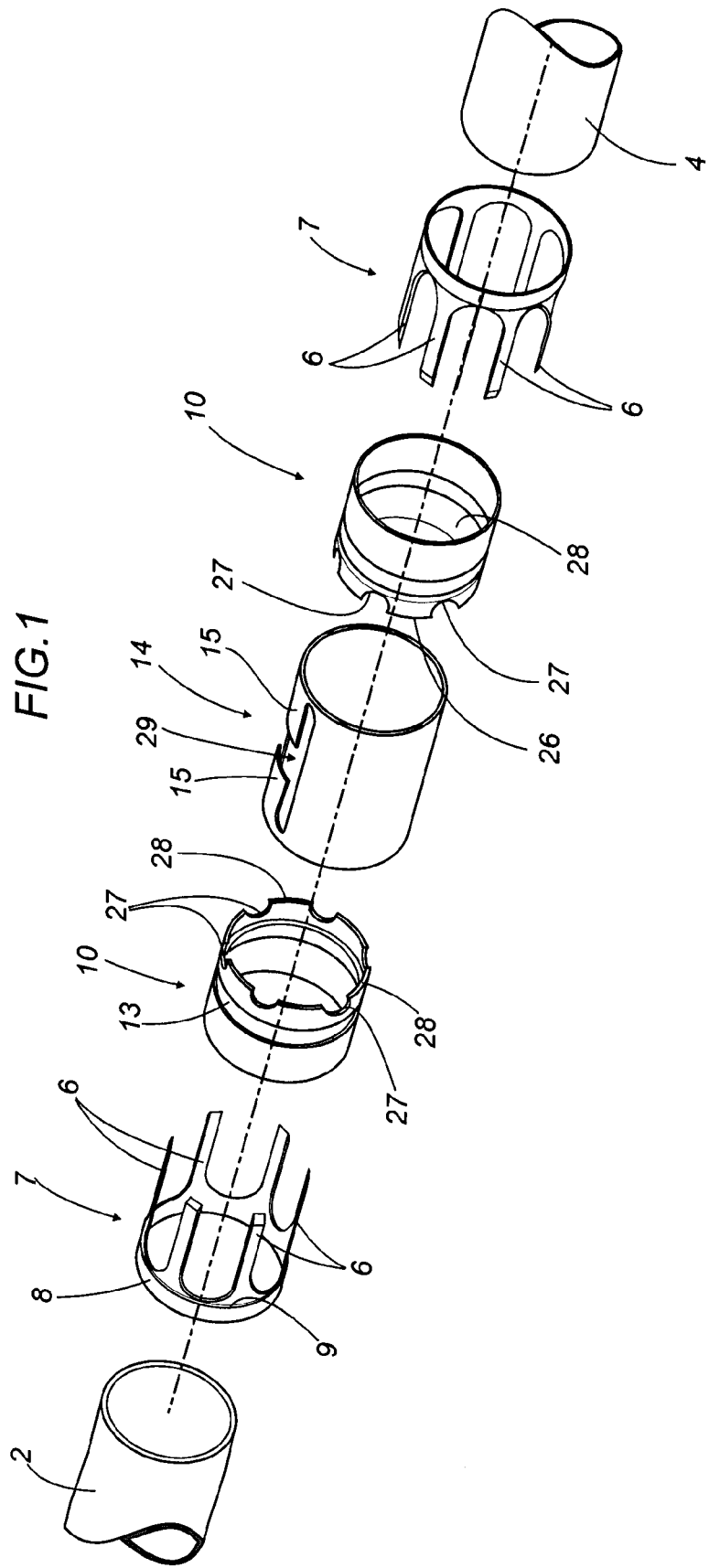
FIG. 1 is an exploded view of an embodiment of the device according to the present invention in an end-to-end application.

With reference to FIG. 1, the numerals 2 and 4 denote a first and a second end portion of a blood vessel wall to be connected by end-to-end anastomosis.

In the embodiments described, the device according to the invention comprises:

at least one first engagement element 7 for grasping one of the end portions 2, 4 of the blood vessel; and at least one second engagement element 10 designed to securely engage a first element 7 applied to a respective end portion 2, 4.

In the embodiment illustrated in FIGS. 1 to 4a, relating to an end-to-end application, the device also comprises a second connecting element consisting of an outer cylinder 14 for reciprocally connecting two second engagement elements 10 applied to the end portions 2, 4 of the vessel.

Looking in more detail, the first or inner engagement element 7 consists of a substantially cylindrical body comprising an uninterrupted ring-shaped part 8 which has a plurality of longitudinal legs 6 protruding from the front of it, preferably equispaced and positioned in such a way as to form an annular protrusion or stop lip 9 on the front surface of the ring 8.

The second or middle engagement element 10 consists of a cylindrical element whose outside diameter is equal to the uninterrupted ring-shaped portion 8 of the cylinder 7 and which preferably has an annular recess 13 made in its outside surface.

Further, the inside diameter of the middle cylinder 10 is such that the latter can precisely slide over the inner cylinder 7 until it comes to a stop against the protrusion 9 and remains locked to the cylinder 7 with slight mechanical interference.

Inside, the cylinder 10 has a tapered profile 28 that converges towards its front portion 26, so that the inside diameter at the free edge of the front portion 26 substantially coincides with the inside diameter of the uninterrupted portion 8 of the inner cylinder 7.

Figure 3:
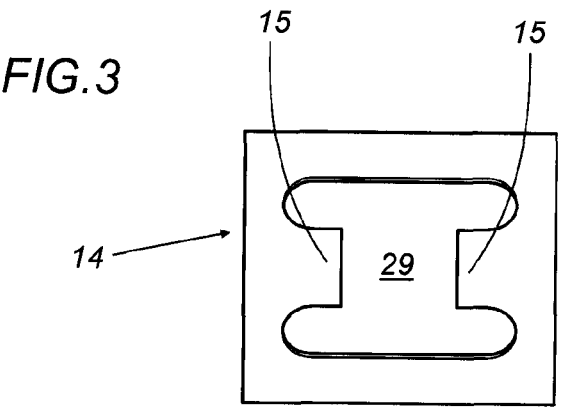
FIG. 3 is a detail view from above showing an outer connecting cylinder of the apparatus of FIGS. 1 and 2.

The outer cylinder 14, shown in more detail in FIG. 3, has an inside diameter that is equal to, or slightly larger than, the outside diameter of the middle cylinder 10, and presents a substantially H-shaped cavity 29, within which there protrude two flexible tabs 15, which converge inwards slightly and are positioned in such a way that, when the outer cylinder is placed over the cylinder 10, the tabs 15 are aligned with, and can snap into, the recess 13.

Figure 2:
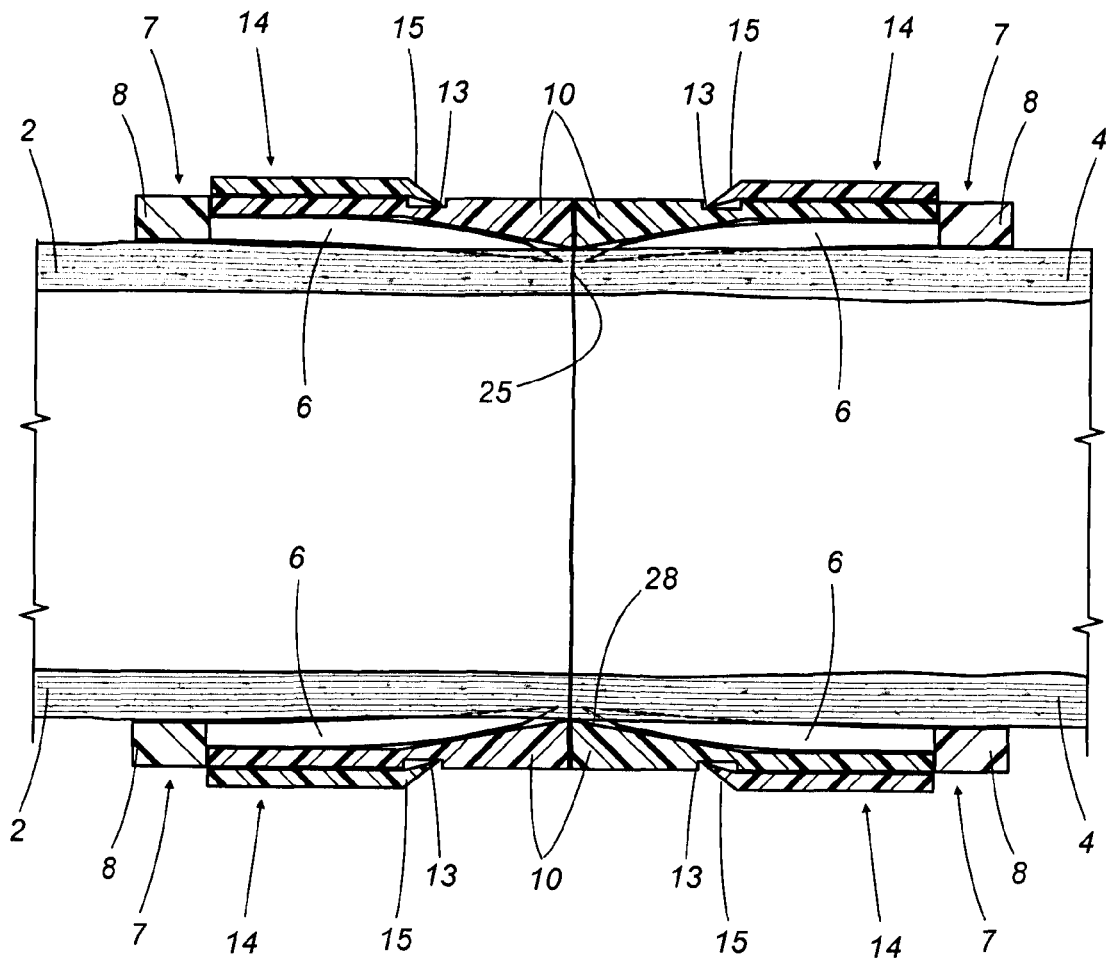
FIG. 2 is a cross section of the apparatus of FIG. 1 in a working configuration.

Described below with reference in particular to FIG. 2 is the configuration of the device applied to two end portions 2, 4 in an end-to-end anastomosis.

In the application configuration of the device, each of the end portions 2, 4 to be connected is inserted into a cylinder 7 with the legs 6 facing the free edge 25 of the vessel wall. To enable the inner cylinders 7 to grasp the end portions 2, 4 of the vessel wall 1, the cylinders 7 are made to slide lengthwise in the middle cylinders 10 in such a way that the legs 6, initially coaxial and parallel to the vessel wall, or slightly divergent, are made to bend inwards by contact with the tapered profile 28 so that they converge towards the inside of each cylinder 7, pressing against the upper surface 24 of the vessel wall 1 and partially penetrating the latter close to the free edge 25.

Advantageously, the depth to which the legs 6 penetrate the vessel wall 1 is determined by the special shape of the legs 6 and of the tapered profile 28 of the cylinder 10, which are so designed that the legs do not go right through the vessel wall, thus avoiding contact between the legs 6 and the blood inside the vessel.

Once the cylinders 7 have been inserted into the cylinders 10, both the end portions 2, 4 are securely fastened by the respective inner cylinder 7 whose legs 6 grasp the vessel walls 1 and which is in turn stably coupled to the middle cylinder 10 by a mechanical interference fit, although it will be understood that the stable coupling between the inner cylinder 7 and the middle cylinder 10 might also be accomplished by bayonet coupling, snap fitting, screw fastening or other suitable fastening means.

At this point, to complete the connection between the portions 2 and 4, it is sufficient to insert the middle cylinders 10 into the two ends of the outer cylinder 14 until the respective tabs 13 snap into the recesses 15 in the cylinders 10.

Under these conditions, illustrated in cross section in FIG. 2, the outer cylinder 14 holds together the middle cylinders 10 which are in turn locked to the inner cylinders 7 grasping the walls 1 of the end portions 2 and 4.

Further, the anastomosed blood vessel has no foreign objects protruding on the inside of it to interrupt the continuity of its lumen, with the advantage of not contaminating the blood or reducing normal blood flow.

Moreover, the legs 6 keep the vessel wall 1 at a precisely measured diameter, which is the same as that of the two end portions 2 and 4 so that the free edges 25 of both coincide exactly and the different layers of the anastomosed vessel tissue are properly healed.

Figure 4A:
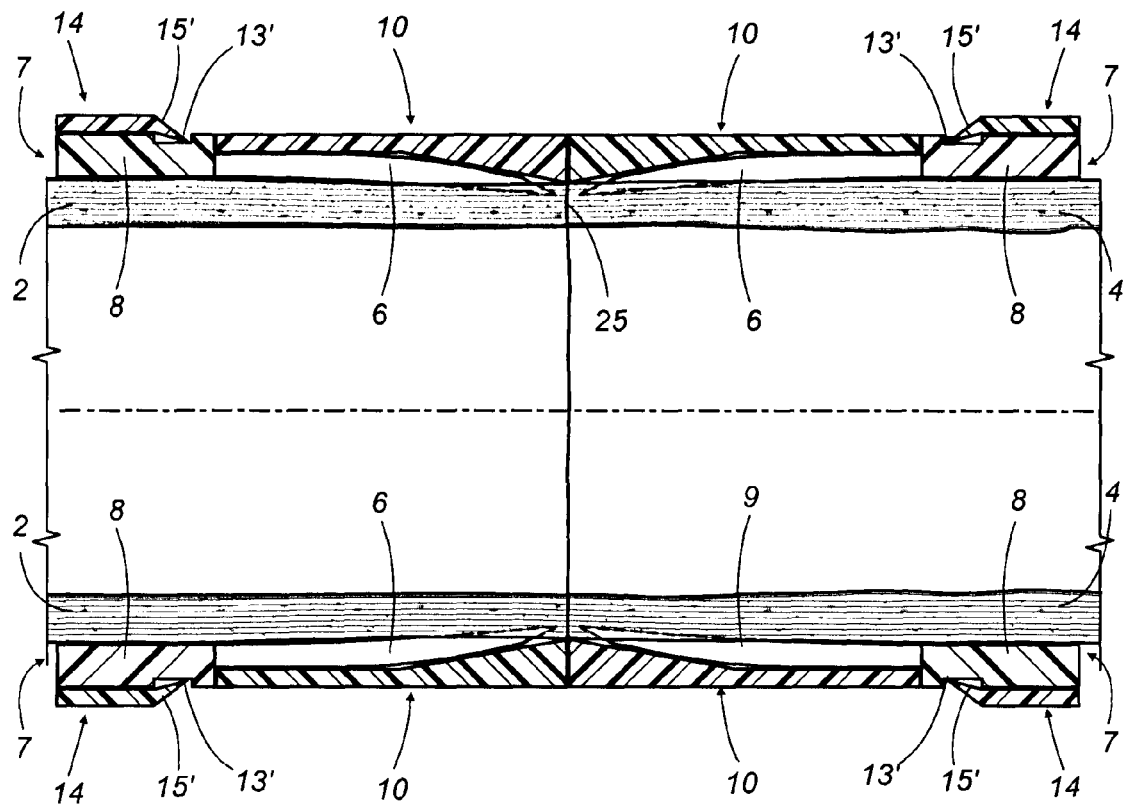
Figure 4B:
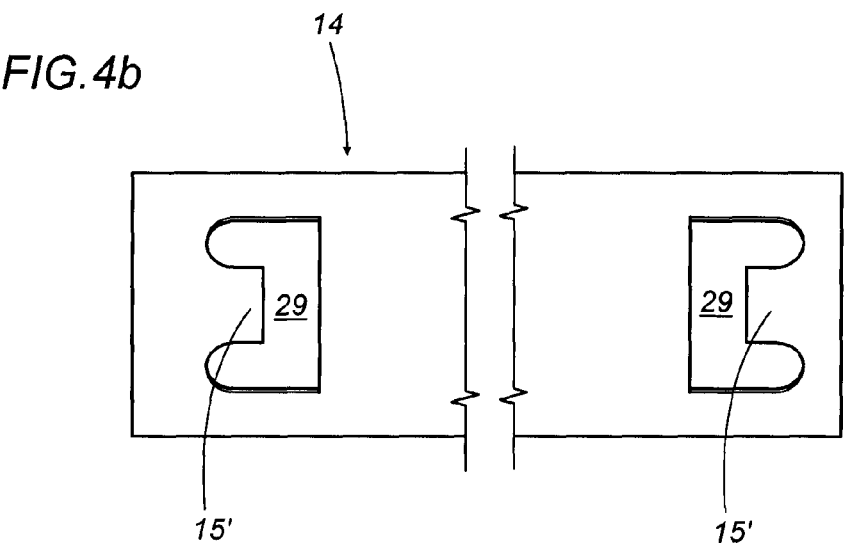

With reference to FIGS. 4a and 4b, the connection between the components of the device may also be made, instead of or in combination with the above, by providing the outer surface of the uninterrupted ring-shaped portion 8 of the inner cylinder 7 with an annular recess 13' similar to the recess 13, combined with tabs 15' (similar to the tabs 15 described above) on the cylinder 14 made at that recess.

In this case, all the components are "packed" in the outer cylinder 14, thus guaranteeing the stability of the connection even in the absence of a stable coupling between the inner cylinder 7 and the middle cylinder 10.

Figure 5A:
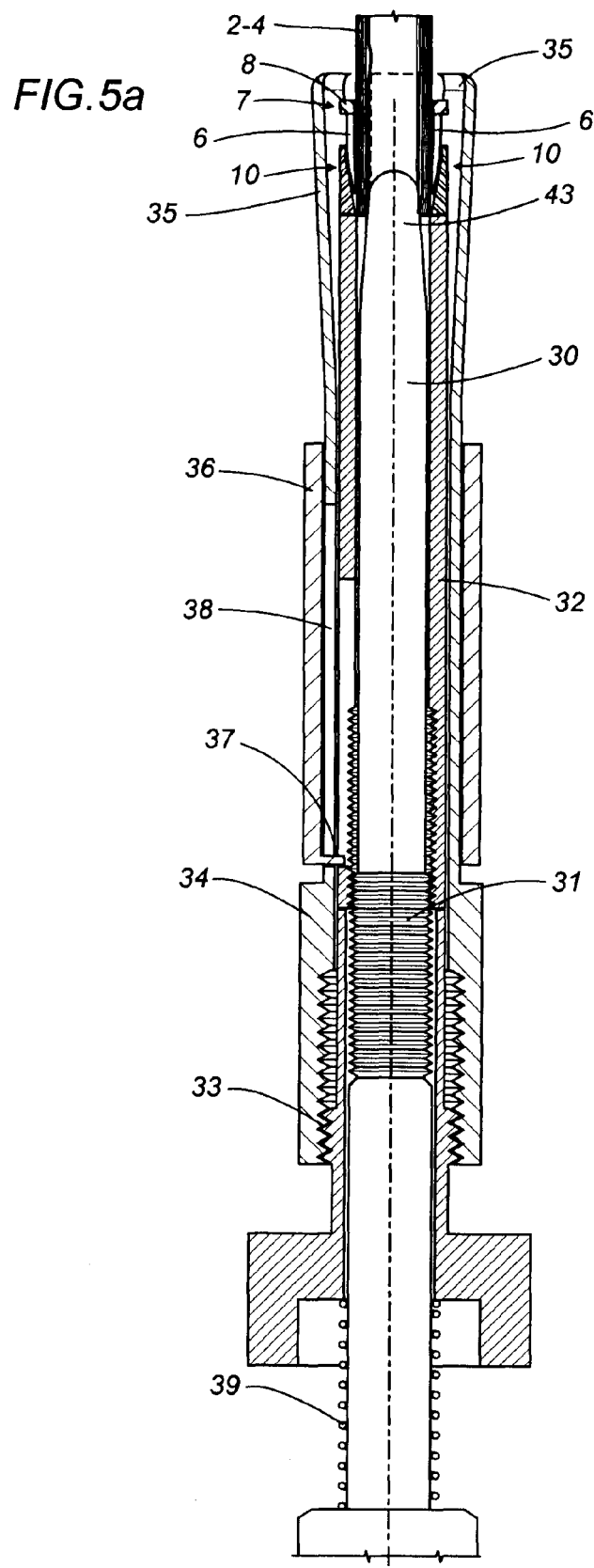
FIGS. 5a and 5b illustrate an applicator for the device according to the invention, the applicator being shown, respectively, in the open configuration and in the closed configuration in which it applies the device to an anastomosed vessel.
Figure 5B:
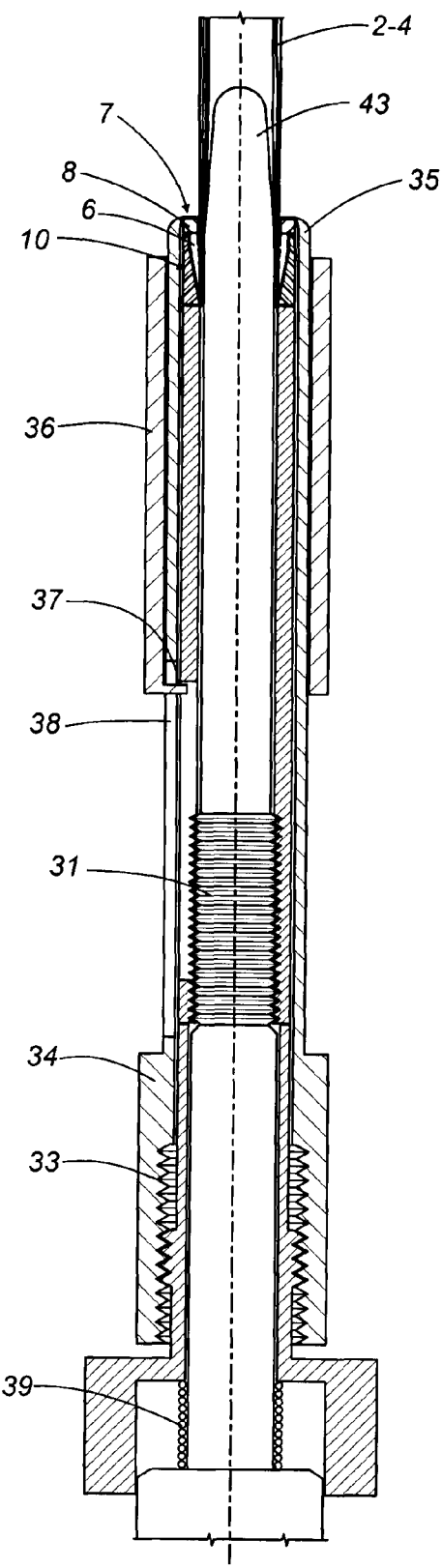
Figure 5C:
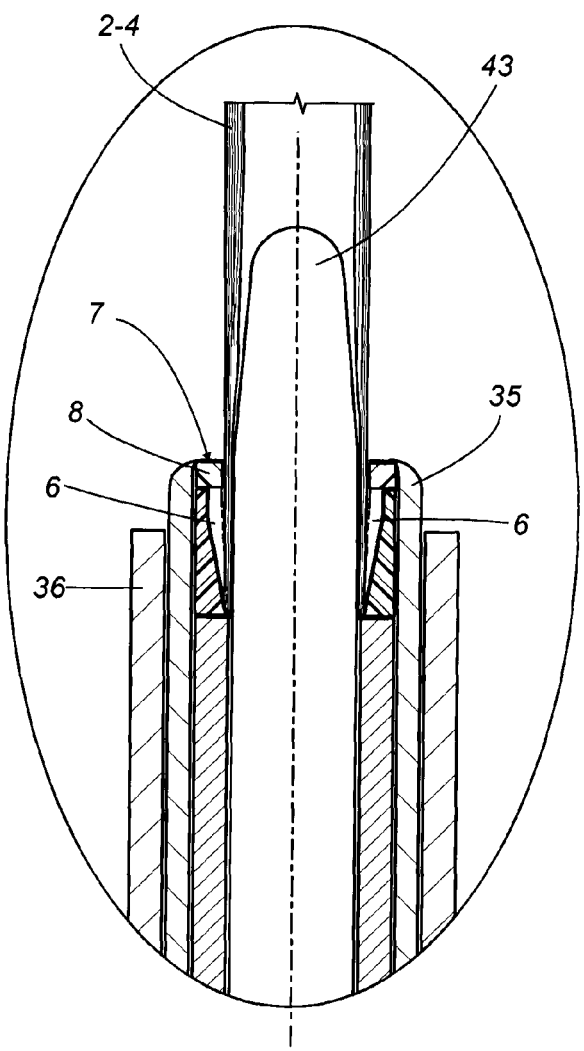
FIG. 5c is an enlarged detail view of FIG. 5b.

Described below with reference to FIGS. 5a, 5b and 5c is an is an applicator apparatus for implanting a device according to the invention to the end portions 2, 4 of a blood vessel.

The applicator comprises a rod 30 which is equipped at one end with a nosepiece 43 of measured diameter and which, by means of a threaded coupling 31, can be screwed into a hollow piston 32 against the action of a spring 39.

The piston 32 is in turn slidable, by means of a second screw coupling 33, inside a hollow body 34, whose top end has a number of flexible tabs 35 normally spread outwards and extending frontally past the nosepiece 43.

A slider 36 can also move on the outside of the hollow body 34, constrained by a tooth 37 that slides in a longitudinal groove 38 made in the body 34.

The slider 36 can adopt a first position in which the tabs are spread apart (FIG. 5a) and a second end position (FIG. 5b) in which the slider has moved towards the end of the body 34 and forced the tabs 35 to converge and close.

To use the applicator, a cylinder 10 is inserted into it through the opening defined by the tabs 35 until the front portion 26 stops against the head 41 of the piston 32.

Next, a first engagement element 7, also referred to herein as a circular staple 7 is partially inserted into the cylinder 10 without forcing and the tabs 35 are closed and positioned at the back in such a way as to hold the ring portion 8 of the circular staple 7.

By operating the applicator, the surgeon inserts a vessel end portion 2 through the circular staple 7 and the cylinder 10 until the edge 25 of the vessel 2 is made to touch on the head 41 of the piston 32.

Preferably, the front portion 26 of the cylinder 10 also has a set of semicircular indentations 27 which, during use, ensure that the vessel end portion 2, 4 to which the device is applied is correctly positioned.

Advantageously, the indentations 27 of the cylinder 10 ensure that the vessel wall has stopped against the piston 32.

By operating on the grip 40 of the rod 30, it is now possible to advance the nosepiece 43 into the vessel 2 in such a way that the vessel remains precisely clamped between the nosepiece 43 itself and the inside surface at the front of the cylinder 10.

The nosepiece is preferably variable in diameter and consists, for example, of a helical wire winding extending in the direction of the rod 30, where the two ends of the helix are fixed to respective elements that can turn relative to each other in such a way so as to move closer together/apart and thus vary the radial dimension of the winding.

By twisting the grip 41 of the piston 32, the surgeon can now advance the piston relative to the tab body so that the tabs and the piston come into contact and clamp the circular staple 7 within the cylinder 10.

As described above, when the legs 6 come into contact with the tapered inside surface 28 of the cylinder 10, they are forced to converge and partially penetrate the vessel wall 2.

Once clamped by the piston 32, the staple 7 is held by interference in the cylinder 10, whilst the vessel wall 2 is retained frontally and radially by the legs 6, with the edge 25 flush with or just protruding from the front 26 of the cylinder 10 and with an internal diameter or lumen defined by the size of the nosepiece 43 used.

At this point, it is sufficient to twist the piston 32 in the opposite direction to retract the slider 36 to open the tabs 35 and release the applicator from the vessel wall.

Once the device has been applied, the vessel end portions 2, 4 have a desired measured diameter thanks to the hold that the legs 6 have on the edge 25. Also, the edge 25 of each of the two end portions remains whole, completely free from external elements, and the vessel protruding elements on the inside of it.

It is evident that, under these conditions, optimum flow is re-established naturally in the blood vessel without external elements or interruptions leading to the above mentioned vessel healing difficulties and to the possible formation of stenosis due to the contact of extraneous elements with the blood.

For reciprocally connecting the two ends 2, 4, provided by the applicator of an engagement device, it is sufficient to apply an outer cylindrical element 14 as described above.

Figure 6:
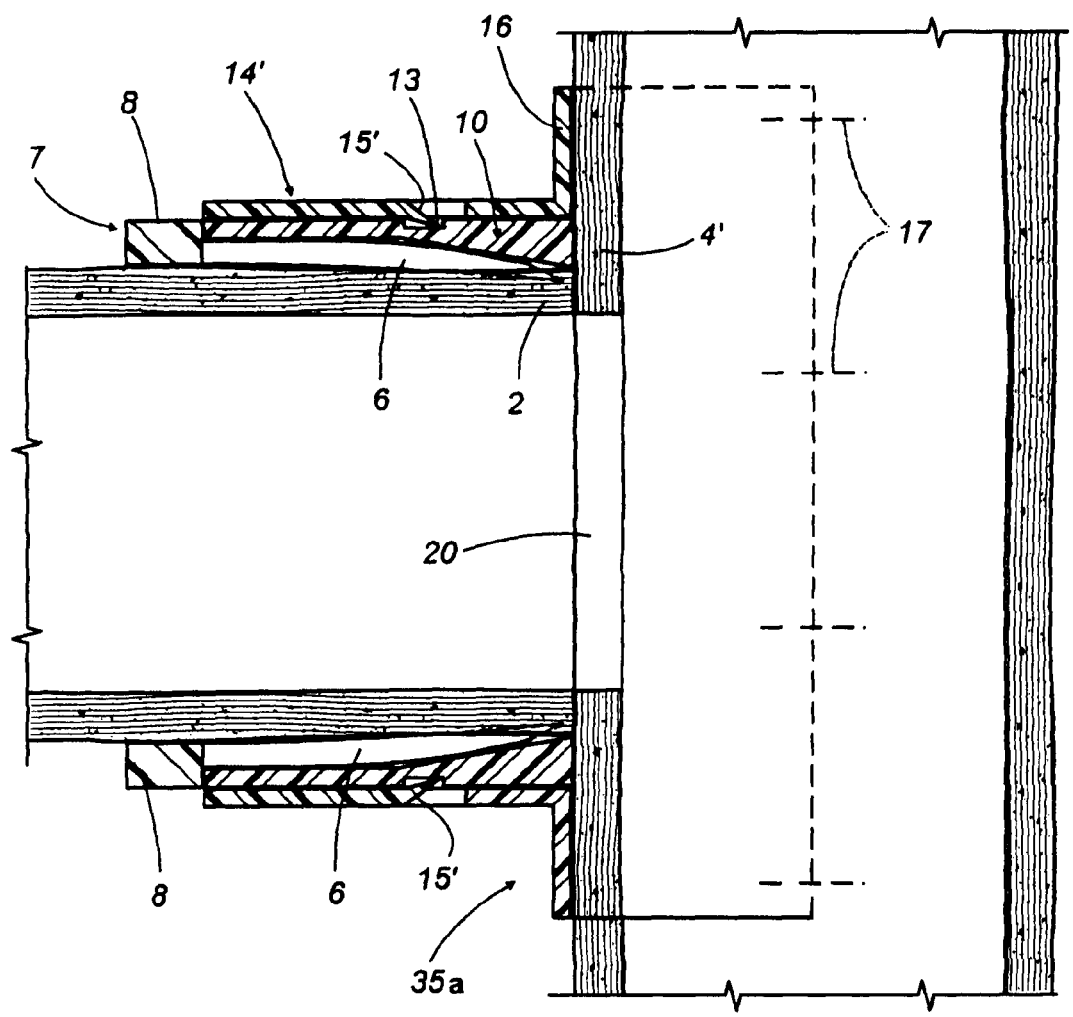
FIG. 6 is a cross section of a device according to the present invention in an end-to-side anastomosis application.

Described below with reference to FIG. 6 is a device according to the invention used for forming an end-to-side anastomosis.

For convenience, where possible, parts corresponding to those described above have assigned to them the same reference numbers as those used above.

In this case, the anastomosis device according to the invention is connected to an end portion 2 of a blood vessel in the same way described above and an applicator like the one already described.

Unlike the above, the outer connecting element consists, in this case, of an outer cylindrical element 14' forming part of a side connecting unit, generically labeled 35a in FIG. 6.

As described above with reference to the connection between the tabs 15 and the recess 13, the element 14' also has elastically deformable tabs 15' designed to snap into the recess 13 in the cylindrical element 10, in order to prevent the end portion 2 from being moved away.

For example, the means for engaging the unit 35a with the vessel wall (which do not in themselves form part of the invention and are therefore not described in detail) may comprise a side connecting element 16 joined stably, either removably or not, to the end connection 14' and designed to be placed at least partially over a side portion 4' of the vessel.

In the schematic example illustrated in FIG. 6, the side element 16 has a central hole 20 which communicates with the element 14' and whose position is such that it can be aligned, during use, with a cut 24 made in the vessel wall 4' by a suitable circular scalpel according to a known method.

The element 16 is equipped with means for fastening it to the portion 4' and consisting for example of fasteners 17, such as metal staples, with or without shape memory, adapted to engage with the wall 4'.

The means for fastening the element 16 to the portion 4' may be of a different type such as, for example, mechanical means (clamps) or glued means.

As stated above, although the invention is especially advantageous for anastomosing blood vessels, the device and the applicator described above may also be used for prosthesis applications.

This invention has been described with reference to preferred embodiments of it but it will be understood that it may be modified and adapted in several ways without thereby departing from the scope of the inventive concept.

What is claimed is:

1. A device for forming an anastomosis of blood vessels having a longitudinal axis and a lumen dimension, said device comprising:

first and second inner cylindrical elements adapted for respectively engaging first and second blood vessel or prosthesis end portions, said first and second inner cylindrical elements each including a ring and a plurality of deformable longitudinal legs extending from the ring;

first and second middle cylindrical elements adapted for being positioned respectively on the first and second blood vessel or prosthesis end portions and into which the first and second inner cylindrical elements are respectively inserted, each of said first and second middle cylindrical elements including a tapered inside surface adapted to bend inward the legs of the respective inner cylindrical element engaged therewith, wherein said first inner cylindrical element is operably engaged with said first middle cylindrical element to define a first engagement element for said first blood vessel or prosthesis end portion;

wherein said second inner cylindrical element is operably engaged with said second middle cylindrical element to define a second engagement element for said second blood vessel or prosthesis end portion;

said device further comprising an outer cylindrical element adapted to receive and retain both said first and second engagement elements, wherein the longitudinal legs are straight and flexible and protrude from the respective rings of said first and second inner cylindrical elements in an axial direction and are directed parallel to an axis of the ring;

wherein the first and second middle cylindrical elements have an inner cylindrical surface defining a cylindrical inside surface adjacent to said tapered inside surface, whereby said cylindrical inside surface guides the legs to slide coaxially and parallel to a wall of the first or second end portions a predetermined length, when the first and second inner cylindrical elements are made to slide in the corresponding first and second middle cylindrical elements, wherein the longitudinal legs are guided initially by the cylindrical inside surface of the respective middle cylindrical elements and subsequently by said tapered inside surface of the respective middle cylindrical element.

2. The device according to claim 1, wherein said first and second engagement elements are retained in said outer cylindrical element by respective first and second snap-fit connections between said outer cylindrical element and said first and second engagement elements.

3. The device according to claim 2, wherein the outer cylindrical element comprises first and second flexible tabs that are received in first and second recesses defined by the first and second middle cylindrical elements, respectively.

4. A device for forming an anastomosis of blood vessels having a longitudinal axis and a lumen dimension, comprising:

a first inner cylindrical element for engaging at least a corresponding first blood vessel or prosthesis end portion in a vicinity of a front edge of the first end portion, said first inner cylindrical element including a ring and a plurality of deformable longitudinal legs with sharp edges which extend from a front of the ring and which are designed to bend inwards during use in such a way as to pierce a wall of the first end portion in the vicinity of the front edge of the first end portion;

a first middle cylindrical element into which the first inner cylindrical element can be inserted, the first middle cylindrical element including an inside surface with a tapered profile that converges towards a front portion thereof so as to bend the legs of the first inner cylindrical element inwards to a predetermined extent;

a second inner cylindrical element for engaging at least a corresponding second blood vessel or prosthesis end portion in a vicinity of a front edge of the second end portion, said second inner cylindrical element including a ring and a plurality of deformable longitudinal legs with sharp edges which extend from a front of the ring and which are designed to bend inwards during use in such a way as to pierce a wall of the second end portion in the vicinity of the front edge of the second end portion;

a second middle cylindrical element into which the second inner cylindrical element can be inserted, the second middle cylindrical element including an inside surface with a tapered profile that converges towards a front portion thereof so as to bend the legs of the second inner cylindrical element inwards to a predetermined extent;

first and second stops connected respectively to said first and second inner cylindrical elements, said first stop adapted to abut said first middle cylindrical element to limit insertion of said first inner cylindrical element into said first middle cylindrical element, and said second stop adapted to abut said second middle cylindrical element to limit insertion of said second inner cylindrical element into said second middle cylindrical element;

means for reciprocally connecting the first and second middle cylindrical elements, said means for reciprocally connecting the first and second middle cylindrical elements comprising a third cylindrical element into which said first and second middle cylindrical elements are adapted to be inserted to stably keep the first end portion in abutment against the second end portion for allowing the first and second end portions to form a continuous blood vessel or prosthesis, said third cylindrical element comprising first and second snap tabs that engage and retain: (i) said first and second inner cylindrical elements, respectively; or, (ii) said first and second middle cylindrical elements, respectively, said first and second snap tabs protruding from a cavity afforded in the third cylindrical element;

the deformable longitudinal legs of the first and second inner cylindrical elements being arranged to only partially penetrate the respective walls of said first and second end portions upon contact between said first and second stops with said respective first and second middle cylindrical elements so as to avoid direct contact between the respective deformable longitudinal legs thereof and blood inside the respective first and second blood vessel or prosthesis and to substantially keep constant during use the respective lumen dimensions of the first and second end portions, wherein the longitudinal legs are straight and flexible and protrude from the respective rings of said first and second inner cylindrical elements in an axial direction and are directed parallel to an axis of the ring;

wherein the first and second middle cylindrical elements have an inner cylindrical surface defining a cylindrical inside surface adjacent to said tapered inside surface, whereby said cylindrical inside surface guides the legs to slide coaxially and parallel to a wall of the first or second end portions a predetermined length, when the first and second inner cylindrical elements are made to slide in the corresponding first and second middle cylindrical elements, wherein the longitudinal legs are guided initially by the cylindrical inside surface of the respective middle cylindrical elements and subsequently by said tapered inside surface of the respective middle cylindrical element.

5. The device according to claim 4, wherein said cavity of the third cylindrical element is H-shaped.

6. The device according to claim 4, wherein said first and second snap tabs are flexible.

7. The device according to claim 4, wherein said first and second snap tabs converge toward the inside of said third cylindrical element.

8. The device according to claim 4, wherein a front portion of each of the first and second middle cylindrical elements includes a set of semicircular indentations made therein.

9. The device according to claim 4, wherein the first and second inner cylindrical elements are adapted to stably engage the respective first and second middle cylindrical elements with mechanical interference.

10. The device according to claim 4, wherein both said first and second middle cylindrical elements can be inserted precisely into the third cylindrical element.

11. The device according to claim 10, wherein the first and second snap tabs protrude into the third cylindrical element, each of said first and second snap tabs arranged to snap into a respective corresponding external annular recess made in an outside surface of either the first or second middle cylindrical elements.

* * * * *

UNITED STATES PATENT AND TRADEMARK OFFICE
CERTIFICATE OF CORRECTION

PATENT NO.        : 8,480,695 B2
APPLICATION NO.   : 12/941301
DATED             : July 9, 2013
INVENTOR(S)       : Enzo Borghi et al.

It is certified that error appears in the above-identified patent and that said Letters Patent is hereby corrected as shown below:

In the Claims:

In claim 4, in column 8, line 52, please delete "use the", and replace it with --use--.

Signed and Sealed this
Eighth Day of October, 2013

Teresa Stanek Rea
*Deputy Director of the United States Patent and Trademark Office*